(12) United States Patent
Robinson

(10) Patent No.: US 8,263,792 B2
(45) Date of Patent: Sep. 11, 2012

(54) BIOMASS REFINING BY SELECTIVE CHEMICAL REACTIONS

(75) Inventor: J. Michael Robinson, Odessa, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 237 days.

(21) Appl. No.: 12/566,427

(22) Filed: Sep. 24, 2009

(65) Prior Publication Data

US 2011/0071306 A1  Mar. 24, 2011

(51) Int. Cl.
*C07D 307/40* (2006.01)
(52) U.S. Cl. ........................................................ 549/483
(58) Field of Classification Search .................... 549/483
See application file for complete search history.

(56) References Cited

U.S. PATENT DOCUMENTS

| | | | | |
|---|---|---|---|---|
| 3,071,599 A | * | 1/1963 | Hales et al. | 549/488 |
| 4,421,856 A | * | 12/1983 | Muller et al. | 435/161 |
| 5,516,960 A | | 5/1996 | Robinson | |
| 5,520,793 A | | 5/1996 | Genders et al. | |

OTHER PUBLICATIONS

HL Chum and RP Oveend, "Biomass and renewable fuels," Fuel Processing Technology 71 (2001) 187-195.
JM Robinson, PT Herndon, PL Holland, LD Marrufo "Regeneration and Recovery of Hydriodic Acid after Reduction of Polyols to Fuels," Organic Process Research & Development 1999, 3, 352-356.
JM Robinson et al., "The use of catalytic hydrogenation to intercept carbohydrates in a dilute acid hydrolysis of biomass to effect a clean separation from lignin," Biomass and Bioenergy 26 (2004) 473-483.
JM Robinson et al., "Electrohydrolysis recycling of waste iodide salts into hydriodic acid for the chemical conversion of biomass into liquid hydrocarbons," Journal of Membrane Science 179 (2000) 109-125.

* cited by examiner

*Primary Examiner* — Taofiq A Solola
(74) *Attorney, Agent, or Firm* — Robert W Strozier

(57) ABSTRACT

A method is disclosed for the acid hydrolysis of carbohydrates in or from biomass, using a solvent system including an aqueous ether, where the ether form a majority of the system, which affords high yields to the platform chemicals such as 2-furfural and 5-hydroxymethylfurfural (5-HMF). The later can also undergo a domino reaction to chemicals including levulinic acid, particularly with oxygenated anions and greater water content. A total dissolution and reaction of biomass occurs under a range of relatively mild conditions (combined Severity range ~2.2-2.6). Lignin and lignin derived products can be easily separated by precipitation.

16 Claims, No Drawings

US 8,263,792 B2

BIOMASS REFINING BY SELECTIVE CHEMICAL REACTIONS

ACKNOWLEDGEMENT

The research was partially supported by the Robert A. Welch Foundation Chemistry Department Research Grant AW-0013.

BACKGROUND OF THE INVENTION

1. Field of the Invention

Embodiments of the present invention relate to catalysts and solvent combinations for hydrolysis and simultaneous dehydrations of carbohydrate containing biomass to afford platform chemicals from the carbohydrates and methods for making and using same.

Embodiments of the present invention relate to catalysts and solvent combinations for hydrolysis and simultaneous dehydrations of carbohydrate containing biomass to afford platform chemicals from the carbohydrates and methods for making and using same, where the method includes hydrolysis and simultaneous dehydration of carbohydrates, while providing a facile separation from lignin and lignin fragments and where the method uses a solvent system comprising an aqueous ether solution and optionally an acid.

2. Description of the Related Art

Present technology cannot achieve cyclo-dehydrations of carbohydrates or other naturally occurring polymers in high yield directly without the use of exotic and often expensive solvents such as ionic liquids (Zhang 2007) or by using dipolar aprotic solvents such as DMSO, which cannot be recovered and leaves undesirable impurities in the products (see US2008/0033188 to Dumesic).

Present technology has not recognized the impact of the counter ions in these reactions to enable different products (i.e., 5-hydroxymethyl-2-furfural (5-HMF) or levulinic acid (LA)) to be produced much less to control the amounts and types of impurities co-produced. HCl for example can selectively produce 5-HMF from the C6 carbohydrate polymers, while $H_2SO_4$ tends to direct the reaction product to LA at the expense of the intermediate 5-HMF.

Weaker acids than these, such as mono-hydrogen sulfate and phosphoric acid that also have weakly nucleophilic counterions, can also allow the reaction to form mainly 5-HMF without the generation of the chloride cleavage product (2-chloroethoxyethanol) resulting from the reaction of the chloride ion (under acidic conditions) with the solvent dioxane. The neutral but reactive 2-chloroethoxyethanol product must also be separated from the final product mix. However, the undesired byproduct, 2-chloroethoxyethanol, can be minimized by careful control of the conditions. For example, weak acid (type of acid and molarity), high substrate loading, and short reaction time all contribute to reactions in which none of this compound is detected. Conversely, a high chloride content with HCl as the acid, at reasonably higher molarity and especially with added chloride salts (especially LiCl), are conditions where dioxane alone affords a new synthesis of the 2-chloroethoxyethanol in high yield that may be of commercial interest.

For the most part, the trend in the industry to make fuels (e.g., ethanol) and platform chemicals (e.g., glucose and xylose) from biomass resources has been to try to avoid the formation of these cyclo-dehydration products, because they were toxic to the fermentation processes used. They were thus deemed as "undesirable degradations." On the other hand, the reason carbohydrates are poor fuels is because they contain too many oxygens, literally with every carbon having an oxygen from the equivalent of a mole of hydrate (water).

Thus, there is a need in the art for improved methods for converting biomass into a variety of useful platform chemicals.

SUMMARY OF THE INVENTION

Embodiments of this invention provide a broad based process to hydrolyze naturally occurring carbohydrates in or from biomass sources into monomeric sugars, which are then rapidly and/or simultaneously converted into several versatile platform chemicals including 2-furfural, 5-hydroxymethylfurfural, and levulinic acid with the co-production of formic acid.

Embodiments of this invention provide a method including contacting a source of hydrolysable carbohydrates in the presence of a solvent system and a dilute acid at a temperature and pressure sufficient to achieve a desired degree of conversion of the hydrolysable carbohydrate polymers, where the solvent system includes an aqueous ether solution such as an aqueous 1,4-dioxane solution. The method can also include cooling the reaction mixture to a desired lower temperature and separating a desired platform chemical or chemicals from the reaction mixture.

Embodiments of this invention relates to methods to convert ethers into chloroalcohols. Solvents in the presence of a weak acid and in the absence of carbohydrates can be converted into Cl compounds. For example, with weakly acidic (type of acid and molarity), high substrate loading, and short reaction time all contribute to reactions were in which none of this compound is detected. Conversely, a high chloride content with HCl as the acid, at reasonably higher molarity and especially with added chloride salts (especially LiCl), are conditions where dioxane alone affords a new synthesis of the 2-chloroethoxyethanol in high yield that may be of commercial interest.

DETAILED DESCRIPTION OF THE INVENTION

The inventor has found that a broad based process to hydrolyze naturally occurring carbohydrates and carbohydrate polymers can be developed, where the carbohydrates and carbohydrate polymers are from biomass resources and the hydrolysis initially yields monomeric sugars, which are then rapidly and simultaneously converted into several versatile platform chemicals. The inventor has found that the abundant biomass carbohydrates and polymeric carbohydrates (hemicellulose, cellulose, and starch) are simultaneously depolymerized to their monomers, i.e., mostly xylose and glucose, respectively, which continue to react and are cyclo-dehydrated to form 2-furfural (2-Fur) and 5-hydroxymethyl-2-furfural (5-HMF).

In typical acid hydrolysis reactions of carbohydrates and carbohydrate polymers in or from biomass, substituting an ether type solvent such as 1,4-dioxane for the majority of the water, changes the course of the reaction. Instead of the usual poor yields of monose sugars of xylose and glucose, the ether solvent system support hydrolysis and simultaneous or rapidly sequential cyclo-dehydrations of these incipient aldoses affording high yields of the platform chemicals 2-Fur and 5-HMF. The later can also undergo a domino reaction to a derivative platform chemical such as levulinic acid, particularly with oxygenated anions and greater water content. A total dissolution and reaction of biomass occurs under a range of relatively mild conditions with a combined severity range between about 2.2 and about 2.6. Lignin and lignin derived products can be easily separated from the platform chemical by precipitation. A softer, step-wise reaction at lower combined severities between about 0.7 and about 1.8 allows selective conversion and dissolution of hemicellulose and lignin while cellulose remains largely unreacted. A simple, soluble sugar like fructose can be converted completely in THF/dilute acid solvent system at a combined severity of about 0.75 to 5-HMF and the acidic water is easily separated and recycled by the addition of fructose to the homogenous reaction solution after cooling. The organic solvents can be evaporated from the platform chemicals and thus recycled. Undesirable chlorinated by-products can be avoided by choices of reagents and conditions.

The inventor has also found that biomass lignin can be totally dissolved and partially or completely depolymerized to form smaller polymeric or oligomeric fragments or phenolic compounds derived from lignin depending upon the severity of the reaction conditions. These lignin derived components can also be re-precipitated to effect almost complete separation from the other platform chemicals.

The direct conversions to platform chemicals from biomass carbohydrates or carbohydrate polymers is accomplished under acidic catalysis conditions in the presence of certain solvent systems such as ether solvents (e.g., 1,4-dioxane) or similar solvents or solvent mixtures. Sequential reactions can be performed with more selective conditions to allow complete separation of hemicellulose derived solutions, which can be converted substantially to the 2-Fur platform chemical, followed by more severe conditions to produce more exclusively the 5-HMF platform chemical. Alternatively, the incipient C6 sugars (e.g., glucose) can be pushed through the 5-HMF (an intermediate in this case) to the derivative platform chemical levulinic acid (LA), along with the concomitant formation of formic acid (FA).

Reactions of the monomeric small sugar molecules, which are very soluble in the reaction media of this invention, at higher initial concentrations, e.g., 40%, allow conditions and parameters to be more readily tested and optimized for subsequent use with the more complex mixture of starting materials that biomass contains. The process breadth includes these more soluble forms of carbohydrates, which would be especially attractive if these monomeric sugars are available as a cost effective feedstock.

More details are available in the examples shown in the six Tables of reactions and five detailed experiments set forth below.

Unique Features of the Invention

A feature of the methods of this invention is the ability to use very dilute acid in an aqueous ether solvent system such as an aqueous 1,4-dioxane solvent system to achieve these hydrolysis products directly without first having to isolate the sugars from the biomass polymers. The reactions of hemicellulose and cellulose each takes place in minutes rather than hours. In certain embodiments, these reactions all occur simultaneously under controlled reaction conditions. The studies of this invention demonstrate that the most difficult biomass carbohydrates to hydrolyze, e.g., the alpha-crystalline cellulose, is not only readily hydrolyzed, but also the incipient sugar, glucose, is automatically converted to the 5-HMF under certain controlled conditions. The strategy of this process is to by-pass production of somewhat unstable monomeric sugars as the final product. Instead, these reactions force the cyclo-dehydration of the produced sugars, as they become available, to their corresponding furan derived products and to thus effect a higher conversion and higher yield the carbohydrates to platform chemicals. The studies presented in this invention also demonstrate that the acid type used determines which platform chemicals from the C6 sugars are formed (either 5-HMF or LA) and how much impact the type and concentration of the counterion (chloride, sulfate, bisulfate, phosphate, etc.) has on the selectivity as well as the purity of the products. The metallic salts studied (including $CuCl_2$ for example) simply hydrolyze in the partially aqueous solution to afford the corresponding proton and counterions depending upon the hard/soft acid/base nature of each salt. In addition, the liberated cation (e.g., $Al^{+3}$) does have some residual Lewis acid catalyst activity.

In experiments with purified alpha-crystalline cellulose (Avicel), total conversions to soluble products were obtained without any char byproduct formation, but a small amount of colored resinous material (humic acids) does occur and to different extents depending on the severity of reaction conditions. Thus, yields approach the theoretical except for these colored moieties and any unreacted sugar at lower severities. These reactions were applied to the individual sugars, xylose, glucose, and fructose as well as the easier to hydrolyze polymer, starch, all with equal success. However, each carbohydrate substrate requires different combined severities of reactions for complete conversion to their respective platform chemicals, and the severity usually has to be increased slightly for a higher load of the substrate. The furan type platform products produced by hydrolysis of whole biomass can be easily separated by sequential distillation or by taking advantage of the fact that 2-Fur is a neutral substance, while 5-HMF is relatively a acidic substance and can be extracted into a basic solution or onto a basic polymer for solid phase extraction. The solvent can be easily removed in vacuo to leave a highly concentrated aqueous solution, which often precipitates solid mixtures.

Furthermore, in contrast to low temperature solvent de-lignifications, which may only partially dissolve lignin from the biomass, the procedures of this invention also simultaneously convert lignin into complex mixtures of small phenolic compounds and can completely dissolve and react the lignin, either simultaneously or sequentially.

Strong concentrations (for example up to 40%) of xylose, glucose and starch have been totally converted demonstrating that the processes of this invention can achieve high conversions at high loading, provided the substrate is dissolved. The processes of this invention also work well on suspended solids as with cellulose and whole biomass (pine). However, whole biomass in granular form (sawdust) has a mechanical limit in the lab of about 15 wt. %, because the wetted mass is a thick slush that is not easily stirred magnetically. Mechanical stirring allows high conversions of a highly loaded slurry, suspension or slush. The acid catalysts may be recycled, depending upon the acid type, and the recycling conditions may vary. For example, in certain embodiments for acids soluble in water, the biomass is washed almost free of salts before reaction or these natural salts may not only partially neutralize some of the acid, but will also contaminate the type of counterion desired in the acid to be recycled.

After the reaction and removal of the solvent such as an aqueous ether solvent (e.g., aqueous dioxane) along with some water in vacuo, all compounds are extracted into a secondary solvent that is essentially immiscible in water (such as methylene chloride). The acidic water layer can be recycled to the next reaction. Alternatively, since such small amounts of acid catalysts are used, these may also simply be neutralized. Dissolved acidic salts behave in the same fashion. In certain embodiments, solid acids are recycled by simple filtration and washing. Purification of the multiple products can also be facilitated by use of certain commercial absorption resins and media. See, e.g., Agar, U.S. Pat. No.

5,788,812. In this manner, removal of small amounts of colored impurities and total extraction from water can be achieved. The neutral 2-furfural (2-Fur) is held less strongly by different media than the relatively acidic 5-hydroxymethyl furfural (5-HMF). The much more acidic levulinic acid (LA) is normally held more strongly to the media. Each can be washed from the various commercially available absorption media to provide these separate platform chemicals. Vacuum distillation as described in the literature can also be used to separate these platform chemicals. Alternatively, more severe conditions with various combinations of acid strength, temperature and residence time allow the incipient C6 carbohydrates to be converted simultaneously into LA and formic acid (FA). These compounds can be simply separated by distillation.

Differences Compared to Prior Art

The processes of this invention, that simultaneously convert incipient sugars via cyclo-dehydration to furan type platform products, begin to alleviate the extra moles of water and thus increase the % C toward the ratio desired for fuels and platform chemicals used to make many other chemicals. In certain embodiments, other even weaker acids and solvents, such as acetic acid, may be used, with the understanding that these acids may be too weak to effect the reactions desired at reasonable temperatures and pressures, may give poorer conversions, and may more difficult to separate from the platform products than the inorganic acids. In other embodiments, other ether type solvents such as tetrahydrofuran (THF) and 2-methyltetrahydrofuran (MTHF) may be used, but are somewhat less effective than a dioxane based solvent system, since they have less miscibility with the water and the polar reagents. The final choice of solvent depends to some degree upon the substrate to be reacted, because these tetrahydrofuran type solvents can assist in separation and purification of the products. For example, with THF as the solvent in a fructose reaction, a partially reacted mixture naturally separates on cooling with only the 5-HMF present in the THF layer, while all the unreacted fructose remains in the lower water layer. Some THF is dissolved in the water layer but only traces of 5-HMF remain. In a similar manner, a THF layer containing product can be effectively separated from the aqueous acid by adding small sugars to effect the selective solvation by the more polar water molecules in a manner similar to a "salting out effect." The addition of a polar sugar accomplishes the saturation of the incipient water layer just as addition of a polar salt would do. The advantage of adding sugar is to avoid buildup and waste disposal of salts whereas the sugar water, which now also recycles the catalyst, can be used for the next reaction while the sugar also serves as the feedstock for the next reaction.

In U.S. Pat. No. 3,071,599 to Hales (1963), a dioxane/water (from 30-95% dioxane) and seven other solvents such as 2-methyl-tetrahydrofuran was used with acid catalysts to dehydrate monomeric hexoses (specifically: fructose, sorbose and glucose) and disaccharides (specifically: sucrose and crude sucrose in the form of high test molasses) to make 5-HMF. However, there was no suggestion to use less than 5% water. The inventor has found, in certain embodiments, that a solvent system having less than 5% water yields a high selectivity to 5-HMF, while solvent systems with higher water concentrations yield a higher selectivity to LA. Instead, U.S. Pat. No. 3,071,599 disclosed but did not claim that his process, like others before him, tried not to drive the reaction to completion, rather to balance the amount of conversion at some point less than complete conversion with a sizable amount of unreacted substrate that would have to be recycled. The prior art did this balancing to preclude the formation of further undesirable products expected with more complete conversions. U.S. Pat. No. 3,071,599 did not specifically recognize the detailed reactivity of some of these solvents with the reagents and did not mention any chlorinated impurities that would be very deleterious to fuels derived there from. Surprisingly, he did have a di(2-chloroethyl)ether as one of the solvents which likely arose as a byproduct of dioxane cleavage initially to 2-chloroethoxyethanol. The alcohol group of 2-chloroethoxyethanol is then more rapidly converted to the symmetrical dichloro compound if sufficient reagent is available.

Only the most inert ether solvents have the least reactivity to give the ring opened chlorinated byproducts. Even traces of chlorinated compounds are highly undesired in fuels. Besides wreaking havoc on the catalyst and equipment in a typical distillation refinery, the hydrochloric acid byproduct from combustion of chlorine containing fuels would be corrosive to the internal combustion engines as well as to the environment. The ketose sugars (fructose and sorbose) are known to be cyclo-dehydrated much easier than the aldose sugars (glucose). However, the ketoses are much more expensive, because they are normally derived from the aldose sugars. In his method, Hales obtained a 42% yield to 5-HMF from glucose (an aldose sugar) using an $AlCl_3$ catalyst at 210° C. Hales did not disclose any biopolymers such as hemicellulose, starch or cellulose, nor did he disclose any 5 carbon sugars such as xylose, that also are the major components of the hydrolysis of hemicellulose polymers in biomass. In contrast to Hales' work, the inventor has demonstrated how to minimize the reaction of dioxane (and other ether solvents) with a chloride containing media to give only traces, if any, 2-chloroethoxyethanol byproduct and yet drive the reaction to completion. The inventor has also demonstrated how to avoid the dioxane (solvents) cleavage reaction to chloro containing products altogether by the use of different counterions present with other acid catalysts. While Hales also disclosed/claimed mineral acids generally, he clearly did not recognize or even suggest the differences that specific counterions of the acids would make and that an entirely different platform chemical (i.e., LA) could result from such specific selection. Hales only viewed these subsequent reactions that consumed 5-HMF as "undesirable byproducts" to be in part avoided by not allowing the reaction to go to completion.

Mednick (*J. Org. Chem.*, 27, 398-403, 1962) also disclosed using a 1/1 mixture of dioxane and water as solvent with the simultaneous combination of weak acids and weak bases to improve the conversion of glucose to 5-HMF, but Mednick's maximum yield was only 46%. Sucrose and starch gave only 44% yield.

Mascal (*Angew Chem. Int. Ed.*, 47, 7924-7926, 2008) disclosed converting glucose and cellulose into the chlorinated analog(s) of 5-HMF using concentrated HCl and added LiCl, which in part confirms that the alcohol functional groups react completely to yield chloro substituted products. However, these halogen containing products must subsequently be de-chlorinated to remove undesirable chlorine to try to make halogen free fuels and platform chemicals. In contrast, this process seeks to at least minimize and by use of alternative reagents to entirely avoid the amount of chlorinated compounds formed whether from substrate sugars/carbohydrates or from the solvents. In this way, this process avoids any subsequent (second step) reaction and the expense associated with removal of chloride as Mascal disclosed.

Levulinic acid has been produced (e.g., U.S. Pat. No. 4,897,497 to Fitzpatrick 1990) in a high temperature (between about 180° C. to about 265° C.) 2 stage treatment of biomass with 1-15% sulfuric acid, but with simultaneous distillation that is a process requirement to simultaneously separate the products as they are forming from the solutions. That process does not use a solvent and thus cannot be concentrated after solvent removal and cannot allow separation of the products by extraction before a distillation step. Lignin is not recoverable for any use other than a burner feedstock, because it is contaminated with considerable char and humic acid products. This is in contrast to the small valuable phenols available by the process of this invention, such as vanillin. Likewise, the Fitzpatrick patent cannot be adjusted to allow the formation of 5-HMF, albeit 2-furfural is produced (<85%) with his 2-stage distillation type reaction. The maximum yields of LA from the Fitzpatrick process is 55%, whereas our process can produce yields approaching theoretical (some small amounts of colored humic acids are formed). In further contrast, our total dissolution reaction of raw biomass is complete in 15 minutes at a temperature of only 170° C. using any one of several acid reagents. Also, the xylose/hemicellulose reactions of this invention are complete to 2-Fur at a temperature between about 120° C. and about 130° C. in 15 minutes or less, and this can be performed sequentially on raw biomass. The fructose (ketose) reactions occur to 100% completion to 5-HMF at much lower severities, e.g., in 0.04 M HCl at 16% loading for 5 minutes at 130° C. This again is in contrast to Hales where he only disclosed temperatures between about 150° C. and about 220° C. Understanding combined severities and solvent effects has allowed us to develop new regions for cyclo-dehydration reactions to occur at lower temperatures, which in turn gives less subsequent decomposition to humic acids, but allows complete conversion to products and selective control to a particular desired product.

Problem(s) Solved

This technology allows for several platform chemicals to be selectively created from the carbohydrates of biomass by selective fractionation reactions and cyclo-dehydrations in this manner. The cost of reagents to affect these transformations is greatly reduced, because very dilute acid solutions are used as well as vacuum flash distillation to recover solvent. In most embodiments of the process of the present process, the solvent is totally miscible with water and aids in dissolving lignin, which the invention believes is important for rapid hydrolysis of all the biopolymers in raw biomass. The energy for these reactions can be provided by either microwave or by conventional heat transfer with no difference in the combined severity required or in the product control or yields. Small batches can be more conveniently reacted via the rapid heat up by microwave methods, while larger batch and continuous flow reactions may use more conventional heating sources. This technology may finally allow for cellulosic biomass processes for a modern biorefinery rather than only using sugar-based or starch-based agricultural crops as feedstock for the ethanol fermentation processes. In this manner, waste crop materials such as corn stover or wood chips from managed forests and even municipal wastes of cardboard, paper, etc. would be suitable feedstock for this versatile hydrolysis process. Thus, human and livestock food chains would not be impacted and this would allow many biomass resources and waste streams to be used to produce fuels and chemicals.

The present process of this invention has the following characteristics: 1) hydrolysis is performed using very dilute acid catalyst for reducing or eliminating the production of chlorinated impurities in a controlled manner; 2) proper choice of acid and counterion can preclude any chlorinated byproduct production, 3) a choice of product (5-HMF vs LA) is allowed by controlled conditions and choice of acid type, 4) high yields, approaching the theoretical, are achievable, 5) fast reactions occur and are completed within minutes, 6) an easy solvent recovery/recycle by flash vacuum distillation is achieved, 7) provides a means to recycle the acid catalyst, 8) provides an easy separation of products from highly concentrated residue or by solvent separation, 9) provides separation of partially reacted lignin polymers and oligomers from the reaction mixture by precipitation, 10) can use either pure feedstocks such as xylose or starch as well as raw biomass such as pine sawdust or even waste biomass streams such as waste paper and crop wastes, and 11) may conduct these reactions in ambient air rather than in an inert atmosphere, although the latter is preferred for safety reasons.

Suitable Reagents

Suitable acids or acid forming reagents for use in this invention include, without limitations, hydrochloric acid (HCl), aluminum trichloride or its hydrates ($AlCl_3$ or $AlCl_3.6H_2O$), sulfuric acid ($H_2SO_4$), hydrogen sulfate salts (such as $NaHSO_4$), aluminum sulfate ($Al_2(SO_4)_3$), phosphoric acid ($H_3PO_4$), phosphotungstic acid (PWA), silicotungstic acid (SiWA), phosphomolybdic acid (PMo), tungstic acid (WA), other multi-valent Lewis acid cation salts such as La, Cu, Co, V, Fe, etc. and mixtures, or salts or combinations thereof.

Suitable sources of hydrolysable carbohydrate polymers include, without limitation, and carbohydrate containing material including hydrolysable carbohydrates and carbohydrate polymers. Exemplary examples of such carbohydrates includes particulate plant matter such as saw dust, grain stalks, sugar cane or beat residue, paper sludge, or any other type of waste high in hydrolysable carbohydrate material such as monosaccharides, disaccharides, trisaccharides, oligosaccharides, polysaccharides, and/or other hydrolysable carbohydrate materials or mixtures or combination thereof.

Suitable heating means include, without limitation, conventional resistive heating elements, microwave heaters, heat transfer heaters, heat exchangers, or other heating devices or mixtures or combinations thereof.

Suitable solvents for use in the invention include, without limitation, cyclic and/or acylic ethers. Exemplary examples include dioxanes such as 1,4-dioxane, tetrahydrofurans, and acyclic ethers, or mixtures or combinations thereof.

Suitable co-solvents for use in the invention include, without limitation, a low molecular weight carboxylic acid. Exemplary examples include C2 to C4 carboxylic acids. C2 to C4 carboxylic acids include formic acid, acetic acid, propanoic acid, butanoic acid, oxalic acid, malonic acid, succinic acid, and other low molecular weight carboxylic acids.

Suitable solvent system include aqueous ether solution, where the ether to water amount varies from about 99% to 60% ether and from about 1% to about 40% water. In other embodiments, the ether to water amount varies from about 95% to 70% ether and from about 5% to about 30% water. In other embodiments, the ether to water amount varies from about 90% to 75% ether and from about 10% to about 25% water.

EXPERIMENTS OF THE INVENTION

Example 1

5-Hydroxymethylfurfural from Fructose in Tetrahydrofuran and HCl

Fructose (5.6 g, 31.1 mmol), 0.5M HCl (5 mL) and THF (30 mL) were mixed to provide a final water concentration of 14%, a substrate loading of 16%, and a total acid concentration of 0.07M. The system was flushed with argon before irradiation in a CEM MARS microwave, XP-1500 Plus pressure controlled Teflon vessel with an RTP-300 Plus temperature probe using the following settings: 2 min ramp to 75 psi followed by a 10 min period at 130° C. with the magnetic stirrer set at medium speed. After cooling to ambient temperature, no separate water layer was observed in the solution indicating an essentially complete reaction. $^{13}$C NMR of this homogeneous solution showed only 5-HMF and solvent THF to confirm this complete reaction.

To achieve a "sugaring out effect" and to separate most of the water and catalyst for recycle, fructose (6 g, 33.3 mmol) was added to the organic solution above. The solution was heated gently for several minutes to assist fructose dissolution, whereupon two layers appeared, a top organic layer and a lower water layer (7.0 mL). The organic layer was separated and dried with $Na_2SO_4$. The $Na_2SO_4$ was washed with $CH_2Cl_2$, which was added to the organic layer. All solvents were removed in vacuo at 38° C. The solid residue (3.7 g, 29.3 mmol) was shown by $^{13}$C NMR to be pure 5-HMF and represents a 94.5% gravimetric yield. A small amount of 5-HMF also remained in the water layer and was simply recycled to the next reaction.

The water layer from the above reaction was re-reacted using approximately the same parameters as the initial fructose reaction. Fructose (2.11 g, 11.7 mmol) was added to the 7 mL recovered water layer to total 8.15 g (44.2 mmol) of fructose. This was mixed with THF (43 mL) to keep a constant 14% water concentration and a 16% loading. The microwave reaction was conducted in the same manner as above with 46 mL of solution resulting, including a 1.25 mL water layer. The separate water layer indicated the reaction was not complete. A $^{13}$C NMR of the organic layer showed, in addition to solvent, 5-HMF (~95%) and a small amount of fructose (~5%). The same product recovery method as above was used to afford pure 5-HMF in a 73.0% yield. Since water is produced as a byproduct of each reaction, a small amount of acid will be required to provide the same concentration of catalyst to maintain the same combined severity and afford the same high yield with each recycle. Alternatively, a small amount of water needs to be removed to adjust the acid concentration and optimize the yield of this recycle reaction.

Example 2

Avicel cellulose (3 g, 18.5 mmol), 1 M HCl (14 mL, 14 mmol), and dioxane (42 mL) were mixed to provide a final water concentration of 25%, a substrate loading of 5.4%, and a total acid concentration of 0.25 M. The solution was irradiated in a CEM MARS microwave, XP-1500 Plus Teflon vessel with an RTP-300 Plus temperature probe using the following settings: 2 min ramp to 190 psi followed by 5 min at 185° C. with the magnetic stirrer set at medium speed. The solution was cooled to ambient temperature. $^{13}$C NMR of this homogeneous solution showed 100% reaction to 5-HMF, but also a relatively equal amount of 2-chloroethoxyethanol (significant peak at ~43 ppm). An extraction of this reaction by the following described procedure also showed ~54% of 2-chloroethoxyethanol relative to the 5-HMF product.
Extraction Procedure To analyze the amount of solvent decomposition, 12 mL of the reaction solution was mixed with 15 mL $H_2O$, and then dioxane was removed in vacuo at 45° C. The remaining water layer was extracted 3 times with 25 mL $CH_2Cl_2$ and concentrated in vacuo at 30° C. to ~3 mL. This concentrated solution was diluted ~1/10 in $CH_2Cl_2$ and analyzed by GC/MS (Agilent Technologies 7890A/5975C).

Comparative Example 3

Pine Sawdust (13.9 g, 35-60 mesh) in 0.27 M HCl (150 mL) was reacted in a Berghoff reactor (250 mL) with a 30 min ramp to the desired temperature and a 60 min period at 130° C. (combined severity=2.10), and cooled quickly in a cold water bath. The solids were filtered and rinsed with 300 mL of $H_2O$ to afford after drying in a vacuum oven, 9.358 g which represents a 33% dissolution and reaction. $^{13}$C NMR showed mainly xylose and glucose and acetic acid, but also ~7% of 2-furfural.

In contrast, the substitution of dioxane for the major part of the solvent and conducting a much less severe (CS=1.26) set of reaction conditions (12% $H_2O$, 10% load, 0.12M HCl, 15 min ramp, 30 min at 124° C.) afforded 78% reaction/dissolution. $^{13}$C NMR showed no sugars and a 14/62/24 ratio of 2-Fur, 5-HMF, and LA, respectively. Lignin content in solution was similarly analyzed and calculated to be 29.6% of the original biomass, which corresponds to substantially complete dissolution and recovery. This allows the estimation that all of the hemi-cellulose and about 16% of the cellulose (amorphous) reacted while mainly the crystalline cellulose (~22%) remained unreacted.

Example 4

Pine sawdust (10.0 g, 35-60 mesh), 1 M HCl (12.5 mL), and dioxane (87.5 mL) were mixed to provide a final water concentration of 12.5% and a total acid concentration of 0.125 M. The system was reacted in a Berghoff reactor (250 mL) with a PTFE liner, using a BAR 945 controller. A Cole Parmer Digi Sense mete with a type K thermocouple was used to measure actual reaction temperature. The heater was preheated to 250° C. whereupon the vessel was lowered into place. Then the heater control could slowly be reduced to provide the desired reaction temperature. This preheating method took 20 minutes and shortened the ramp time to reaction temperature. The reaction was 15 min at 170° C. Cooling was then achieved as quickly as possible in a cold water bath before filtering. Sequential acetone, water, acetone rinses of 250 mL each to afford a final weight of 0.26 g dry weight (97% dissolution-reaction). $^{13}$C NMR allowed the ratios of the three products: 55% 5-HMF, 30% furfural, and 15% levulinic acid. GC/MS analysis showed additionally a 7.2% solvent decomposition into 2-chloroethoxyethanol.

Example 5

Another reaction following similar procedure but in which the temperature was reduced to 112° C. and the reaction time increased to 60 min gave a final weight of 3.94 g or a 58% dissolution-reaction. $^{13}$C NMR ratios showed only two products: δ 5-HMF and 35% furfural with no xylose or glucose detected. GC/MS analysis also shows 0.35% of solvent decomposition into 2-chloroethoxyethanol, relative to these furan products. Precipitation of lignin from a portion of the solution allowed analysis of 26.2% of the original biomass was dissolved and thus isolated as lignin or lignin derived solids. The difference between the lignin and the total percent reaction-dissolution is 31.4%, representing mainly the amount of hemicellulose.

TABLE I

Data for Hydrolysis of Xylose

| Entry | Acid | M | H$_2$O | load | min | °C. | CS[i] | % F[ii] | % CEE[iii] |
|---|---|---|---|---|---|---|---|---|---|
| 1 | HCl | 0.041 | 13% | 40% | 5 | 175 | 1.52 | 100% | 0 |
| 2[iv] | HCl | 0.125 | 10% | 10% | 15 | 130 | 1.16 | 100% | 0.22 |
| 3 | AlCl$_3$ | 0.032 | 14% | 16% | 5 | 170 | 1.26 | 100% | 0 |
| 4 | H$_2$SO$_4$ | 0.063 | 13% | 40% | 5 | 185 | 2.00 | 100% | |
| 5 | NaHSO$_4$ | 0.25 | 13% | 8% | 5 | 195 | 2.89 | 100% | |
| 6 | SiWA[v] | | 10% | 10% | 15 | 195 | | 100% | |
| 7 | PMo[vi] | | 10% | 10% | 15 | 195 | | 100% | |
| 8 | PWA[vii] | | 10% | 10% | 15 | 195 | | 100% | |
| 9 | H$_3$PO$_4$ | 0.625 | 13% | 8% | 5 | 185 | 3.20 | 100% | 0[viii] |

[i]Combined Severity;
[ii]Percent Furfural by $^{13}$C NMR;
[iii]Percent 2-chloroethoxyethanol;
[iv]Conventional heat in a Berghof reactor;
[v]Silicotungstic acid 0.2 w/v %;
[vi]Phosphomolybdic acid 0.2 w/v %, and
[vii]Phosphotungstic acid 2 w/v %.

TABLE II

Data for Hydrolysis of Glucose and Fructose

| Entry | Acid | M | H$_2$O | load | min | °C. | CS | % H[ix] | % L[x] | % Total[xi] | % CEE |
|---|---|---|---|---|---|---|---|---|---|---|---|
| 10[xii] | HCl | 0.143 | 14% | 16% | 5 | 186 | 2.39 | 86 | 14 | 100 | 1.7 |
| 11[xii] | H$_2$SO$_4$ | 0.143 | 14% | 16% | 5 | 184 | 2.33 | 20 | 75 | 95 | |
| 12[xii] | NaHSO$_4$ | 0.286 | 14% | 16% | 10 | 185 | 2.96 | 50 | 26 | 76 | |
| 13[xii] | H$_3$PO$_4$ | 1.43 | 14% | 16% | 10 | 200 | 4.10 | 72 | 19 | 91 | |
| 14[xiii] | HCl | 0.036 | 14% | 16% | 5 | 130 | 0.14 | 100 | 0 | 100 | 0 |
| 15 | HCl | 0.036 | 14% | 16% | 5 | 130 | 0.14 | 100 | 0 | 100 | 0.25 |
| 16 | H$_2$SO$_4$ | 0.036 | 14% | 16% | 5 | 148 | 0.66 | 97 | 2 | 100 | |
| 17 | NaHSO$_4$ | 0.286 | 14% | 16% | 5 | 169 | 2.19 | 93 | 7 | 100 | |

[ix]Percent 5-hydroxymethyl-2-furfural by $^{13}$C NMR,
[x]Percent levulinic acid by $^{13}$C NMR,
[xi]Total % F and % L; difference from 100% shows the amount of unreacted sugar present;
[xii]Glucose reaction; and
[xiii]Reaction was conducted under argon atmosphere.

TABLE III

Data for Hydrolysis of Starch

| Entry | Acid | M | H$_2$O | load | min | °C. | CS | % H | % L | % Total | % CEE |
|---|---|---|---|---|---|---|---|---|---|---|---|
| 18 | AlCl$_3$ | 0.03 | 8% | 40% | 5 | 210 | 2.46 | 91 | 3 | 94 | 0.11 |
| 19[xiv] | HCl | 0.02 | 14% | 16% | 10 | 197 | 2.09 | 56 | 44 | 100 | 20.5 |
| 20 | HCl | 0.08 | 8% | 40% | 5 | 210 | 2.81 | 77 | 12 | 89 | 0.47 |
| 21 | HCl | 0.143 | 14% | 16% | 10 | 196 | 2.98 | 65 | 25 | 90 | 11.9 |
| 22 | H$_2$SO$_4$ | 0.04 | 7% | 5% | 5 | 197 | 2.12 | 50 | 50 | 100 | |
| 23 | H$_2$SO$_4$ | 0.5 | 25% | 32% | 5 | 175 | 2.61 | 0 | 100 | 100 | |
| 24 | NaHSO$_4$ | 0.286 | 14% | 5% | 5 | 195 | 2.95 | 45 | 44 | 89 | |
| 25 | Al$_2$(SO$_4$)$_3$ | 0.04 | 14% | 10% | 15 | 197 | 2.62 | 75 | 25 | 100 | |
| 26 | PWA[vii] | | 10% | 10% | 15 | 195 | | 0 | 91 | 91 | |
| 27[xv] | H$_3$PO$_4$ | 0.286 | 14% | 16% | 5 | 200 | 3.10 | 86 | 14 | 100 | 0.53 |
| 28 | H$_3$PO$_4$ | 0.714 | 14% | 9% | 15 | 208 | 4.21 | 85 | 0 | 85 | 0 |

[xiv]LiCl 0.6 wt % was added to the reaction and

[xv]NaCl 0.4 wt % was added to the reaction.

TABLE IV

Data for Hydrolysis of Cellulose

| Entry | Acid | M | $H_2O$ | load | min | °C. | CS | % Rxn[xvi] | % H | % L | % Total | % CEE |
|---|---|---|---|---|---|---|---|---|---|---|---|---|
| 29 | HCl | 0.071 | 7% | 5% | 5 | 185 | 2.06 | 90 | 100 | 0 | 100% | 9.14 |
| 30 | HCl | 0.071 | 14% | 5% | 5 | 195 | 2.35 | 99 | 87 | 13 | 100% | 0.47 |
| 31 | HCl | 0.25 | 25% | 5% | 5 | 185 | 2.60 | 100 | 0 | 100 | 100% | 58.1 |
| 32 | HCl | 0.143 | 7% | 32% | 5 | 203 | 2.89 | 95 | 81 | 13 | 94% | 4.4 |
| 33[iv] | HCl | 0.125 | 13% | 10% | 15 | 170 | 2.33 | 97 | 89 | 11 | 100% | 8.09 |
| 34 | $AlCl_3$ | 0.094 | 14% | 11% | 5 | 203 | 2.71 | 97 | 95 | 5 | 100% | 1.56 |
| 35 | $H_2SO_4$ | 0.037 | 7 | 16% | 10 | 200 | 2.51 | 99 | 51 | 49 | 100% | |
| 36 | $H_2SO_4$ | 0.071 | 14 | 16% | 5 | 200 | 2.50 | 100 | 35 | 65 | 100% | |
| 37 | $H_2SO_4$ | 0.571 | 29 | 16% | 10 | 180 | 3.11 | 99 | 0 | 100 | 100% | |
| 38 | $H_3PO_4$ | 1.071 | 14 | 16% | 10 | 200 | 3.97 | 66 | 62 | 8 | 70% | |

[xvi]The percent reaction/dissolution of the cellulose was determined by filtration of unreacted solids.

TABLE V

Data for Hydrolysis of Pine

| Entry | Acid | M | $H_2O$ | load | min | °C. | CS | % Rxn | % F | % H | % L | % Total | % CEE |
|---|---|---|---|---|---|---|---|---|---|---|---|---|---|
| 39[iv] | HCl | 0.125 | 13% | 10% | 15 | 130 | 1.16 | 66 | 56 | 26 | 0 | 82% | 3.1 |
| 40[iv] | HCl | 0.125 | 13% | 10% | 60 | 112 | 1.23 | 58 | 35 | 65 | 0 | 100% | 0.35 |
| 41[iv] | HCl | 0.125 | 13% | 10% | 15 | 170 | 2.33 | 97 | 31 | 57 | 12 | 100% | 7.2 |
| 42[iv] | HCl | 0.06 | 13% | 10% | 15 | 190 | 2.62 | 99 | 23 | 67 | 0 | 100% | 4.07 |
| 43[iv] | $H_2SO_4$ | 0.25 | 13% | 10% | 15 | 170 | 2.63 | 97 | 11 | 0 | 89 | 100% | |
| 44[iv] | $H_3PO_4$ | 0.25 | 13% | 10% | 15 | 195 | 3.37 | 69 | 36 | 44 | 0 | 80% | |
| 45 | $AlCl_3$ | 0.02 | 50% | 20% | 15 | 185 | 1.85 | 100 | 29 | 51 | 20 | 100% | 1.31 |
| 46 | $H_2SO_4$ | 0.04 | 14% | 10% | 5 | 200 | 2.27 | 100 | 26 | 51 | 23 | 100% | |
| 47 | HCl | 0.143 | 14% | 10% | 10 | 170 | 2.22 | 100 | 24 | 64 | 12 | 100% | 8.6 |

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

I claim:

1. A process to hydrolyze naturally occurring carbohydrates in or from biomass sources into versatile platform chemicals, where the process comprises the step of:
   contacting a source of naturally occurring carbohydrates with an acid in the presence of a solvent system comprising from about 60 to 99% of an ethereal solvent, from about 1 to 40% of water, and a co-solvent comprising a $C_2$ to $C_4$ carboxylic acid at a temperature and pressure and for a time sufficient to form monomeric sugars, which are then rapidly and/or simultaneously converted into a platform chemical or a plurality of platform chemicals, where an acid concentration is between about 0.02 M and about 1 M and where the platform chemicals include 2-furfural, 5-hydroxymethylfurfural, and levulinic acid with the co-production of formic acid, or mixtures or combinations thereof.

2. The process of claim 1, wherein the monomeric sugars are selected from the group consisting of glucose, mannose, galactose, fructose, sorbose, xylose, ribose, arabinose, and mixtures or combinations thereof.

3. The process of claim 1, wherein the ethereal solvent is selected from the group consisting of tetrahydrofurans, dioxanes, acyclic ethers and mixtures or combinations thereof.

4. The process of claim 1, wherein the acid is selected from the group consisting of formic acid, acetic acid, propanoic acid, and mixtures or combinations thereof.

5. The process of claim 1, further comprising the step of:
   pre-treating the source with a pretreating solution to remove salts, extractive, protein or lignin.

6. The process of claim 1, further comprising the step of:
   cooling the reaction mixture to a desired lower temperature.

7. The process of claim 1, further comprising the step of:
   separating the platform chemical or chemicals from the reaction mixture.

8. The process of claim 1, wherein the reaction mixtures is heated using a resistive heater system, a microwave heating system, a heat transfer system, a heat exchange system or a combination of these heating systems.

9. The process of claim of claim 7, wherein sugars are added to the cooled reaction mixture to cause more effective separation of the solvent/water layers.

10. A method comprising contacting a source of hydrolysable carbohydrate material in the presence of a solvent system comprising from about 60 to 99% of an ethereal solvent, from about 1 to 40% of water, and , a co-solvent comprising a $C_2$ to $C_4$ carboxylic acid and an acid at a temperature and pressure and for a time sufficient to achieve a desired degree of conversion of the hydrolysable carbohydrate polymers into monomeric sugars, which are then rapidly and/or simultaneously converted into to desired platform chemical or plurality of platform chemicals, where an acid concentration is between about 0.02 M and about 1 M and where the platform chemicals include 2-furfural, 5-hydroxymethylfurfural, and levulinic acid with the co-production of formic acid, or mixtures or combinations thereof.

11. The method of claim 10, wherein the ethereal solvent is selected from the group consisting of tetrahydrofurans, dioxanes, acyclic ethers, and mixtures or combinations thereof.

12. The method of claim 10, wherein the acid co-solvent is selected from the group consisting of formic acid, acetic acid, propanoic acid, and mixtures or combinations thereof.

13. The method of claim 10, further comprising the step of: pre-treating the source with a pretreating solution to remove salts, extractive, protein or lignin.

14. The method of claim 10, further comprising the step of: cooling the reaction mixture to a desired lower temperature.

15. The method of claim 10, further comprising the step of: separating a desired platform chemical or chemicals from the reaction mixture.

16. The method of claim 10, wherein the reaction mixtures is heated using a resistive heater system, a microwave heating system, a heat transfer system, a heat exchange system or a combination of these heating systems.

* * * * *